US011331159B2

(12) United States Patent
Wang

(10) Patent No.: US 11,331,159 B2
(45) Date of Patent: May 17, 2022

(54) OPERATING LAMP AND METHOD FOR ADJUSTING OPERATING FIELD LIGHT SPOTS THEREOF

(71) Applicant: NANJING MINDRAY BIO-MEDICAL ELECTRONICS CO., LTD., Nanjing (CN)

(72) Inventor: Lei Wang, Shenzhen (CN)

(73) Assignee: NANJING MINDRAY BIO-MEDICAL ELECTRONICS CO., LTD., Nanjing (CN)

( * ) Notice: Subject to any disclaimer, the term of this patent is extended or adjusted under 35 U.S.C. 154(b) by 30 days.

(21) Appl. No.: 16/920,707

(22) Filed: Jul. 4, 2020

(65) Prior Publication Data

US 2020/0330178 A1 Oct. 22, 2020

Related U.S. Application Data

(63) Continuation of application No. PCT/CN2018/079883, filed on Mar. 21, 2018.

(51) Int. Cl.
*A61B 90/30* (2016.01)
*A61B 90/35* (2016.01)
(Continued)

(52) U.S. Cl.
CPC ............. *A61B 90/30* (2016.02); *A61B 90/35* (2016.02); *F21S 8/00* (2013.01); *F21V 23/003* (2013.01);
(Continued)

(58) Field of Classification Search
CPC ...... A61B 90/30; A61B 90/35; H05B 47/155; H05B 47/175; F21S 8/00; F21S 2/00;
(Continued)

(56) References Cited

U.S. PATENT DOCUMENTS

| | | | |
|---|---|---|---|
| 3,437,803 A * | 4/1969 | Schafer | .................. G03B 15/02 362/8 |
| 7,922,347 B2 | 4/2011 | Kaletin et al. | |

(Continued)

FOREIGN PATENT DOCUMENTS

| | | |
|---|---|---|
| CN | 101257856 A | 9/2008 |
| CN | 202188383 U | 4/2012 |

(Continued)

OTHER PUBLICATIONS

Extended European Search Report issued in related European Application No. 18910806.1, dated Nov. 3, 2020, 11 pages.
(Continued)

*Primary Examiner* — Tsion Tumebo
(74) *Attorney, Agent, or Firm* — Bayes PLLC

(57) ABSTRACT

An operating lamp and a method for adjusting light spots in an operating field of an operating lamp are disclosed. The operating lamp includes a first lighting unit, a second lighting unit, and a control unit. A light beam emitted by the first lighting unit forms a first light spot having a first equivalent diameter in an operating field, and the first light spot have a light distribution that meets an operating lamp standard. A light beam emitted by the second lighting unit forms a second light spot having a second equivalent diameter in the operating field, and the second light spot have a light distribution that does not meet the operating lamp standard. The second equivalent diameter is greater than the first equivalent diameter. The control unit is configured to control working states of the first lighting unit and the second lighting unit, and enable the operating lamp to provide the first light spot or a synthetic light spot having a light distribution that meets the operating lamp standard and is formed by the first light spot and the second light spot.

17 Claims, 9 Drawing Sheets

(51) Int. Cl.
  *H05B 47/155* (2020.01)
  *F21S 8/00* (2006.01)
  *F21V 23/00* (2015.01)
  *F21W 131/205* (2006.01)

(52) U.S. Cl.
  CPC ..... *H05B 47/155* (2020.01); *F21W 2131/205* (2013.01)

(58) Field of Classification Search
  CPC . F21V 23/003; F21V 23/04; F21W 2131/205; F21Y 2113/00
  See application file for complete search history.

(56) References Cited

U.S. PATENT DOCUMENTS

| | | | | |
|---|---|---|---|---|
| 2008/0247163 | A1* | 10/2008 | Chen | F21V 14/06 362/237 |
| 2009/0318771 | A1 | 12/2009 | Marka et al. | |
| 2012/0134155 | A1* | 5/2012 | Wendt | H05B 47/10 362/249.03 |
| 2014/0066722 | A1* | 3/2014 | Marka | A61B 17/52 600/249 |
| 2016/0317244 | A1 | 11/2016 | Jacobi | |
| 2017/0030573 | A1* | 2/2017 | Alexanderson | G01S 15/88 |
| 2017/0318641 | A1 | 11/2017 | Yadav et al. | |

FOREIGN PATENT DOCUMENTS

| | | |
|---|---|---|
| CN | 102458016 A | 5/2012 |
| CN | 102563456 A | 7/2012 |
| CN | 102927506 A | 2/2013 |
| CN | 103109127 A | 5/2013 |
| CN | 103162190 A | 6/2013 |
| CN | 103403442 A | 11/2013 |
| CN | 104819389 A | 8/2015 |
| CN | 104819403 A | 8/2015 |
| EP | 2065634 A1 | 6/2009 |

OTHER PUBLICATIONS

International Search Report issued in corresponding International Application No. PCT/CN2018/079883, dated Dec. 25, 2018, 6 pages.

Office Action issued in related Chines Application No. 201880001691.3, dated Mar. 2, 2020, 8 pages.

* cited by examiner

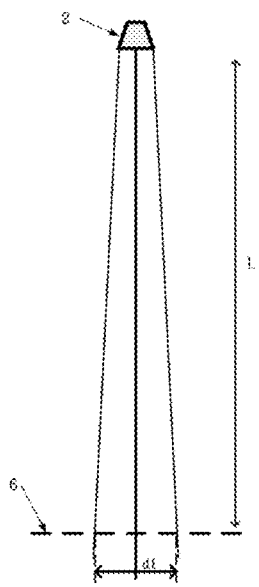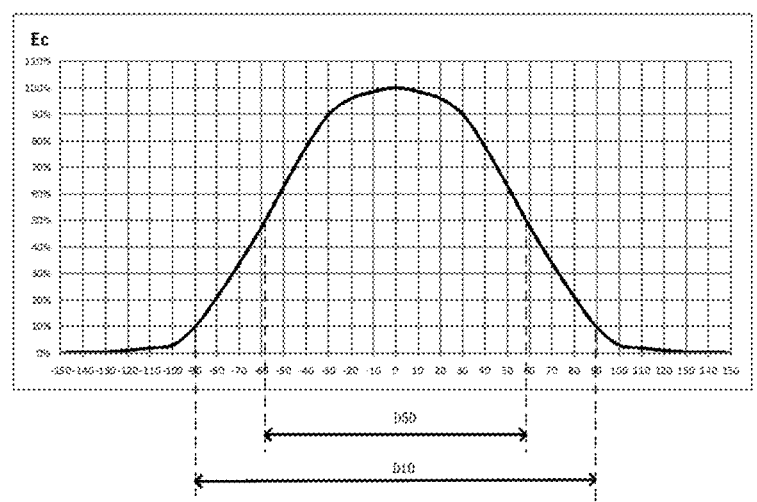
Fig. 2a　　　　　　　　　　Fig. 2b
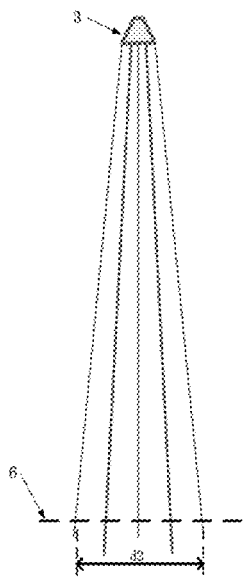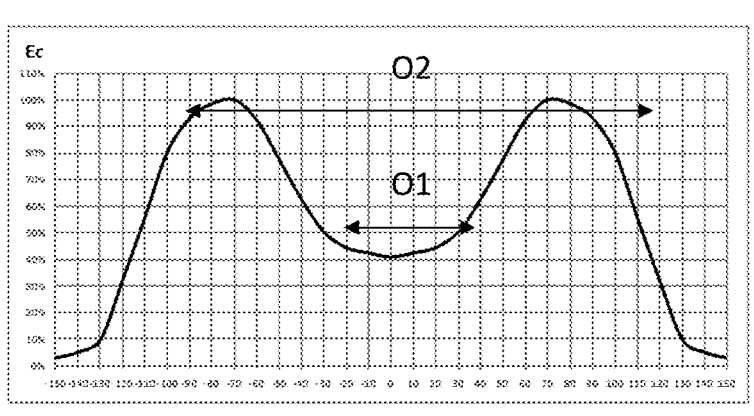
Fig. 3a　　　　　　　　　　Fig. 3b

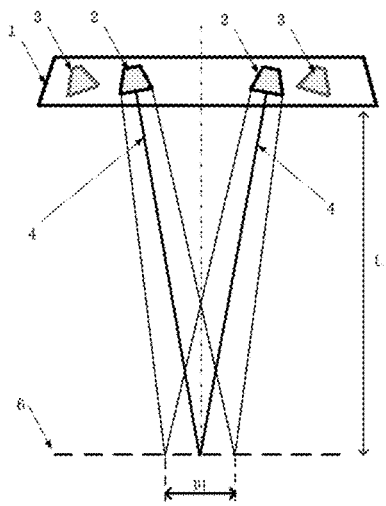
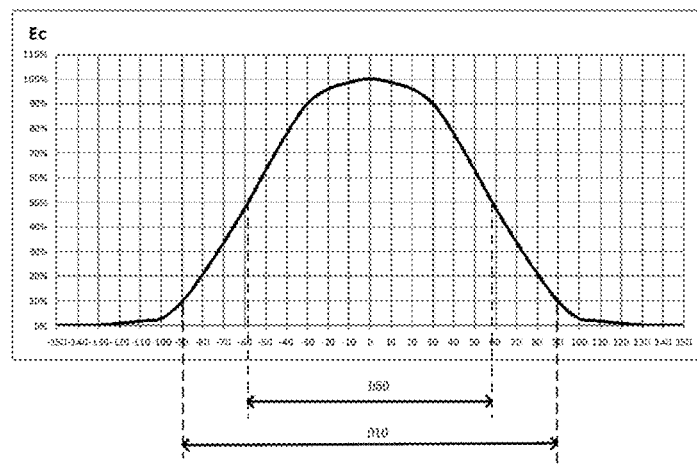
Fig. 4a    Fig. 4b
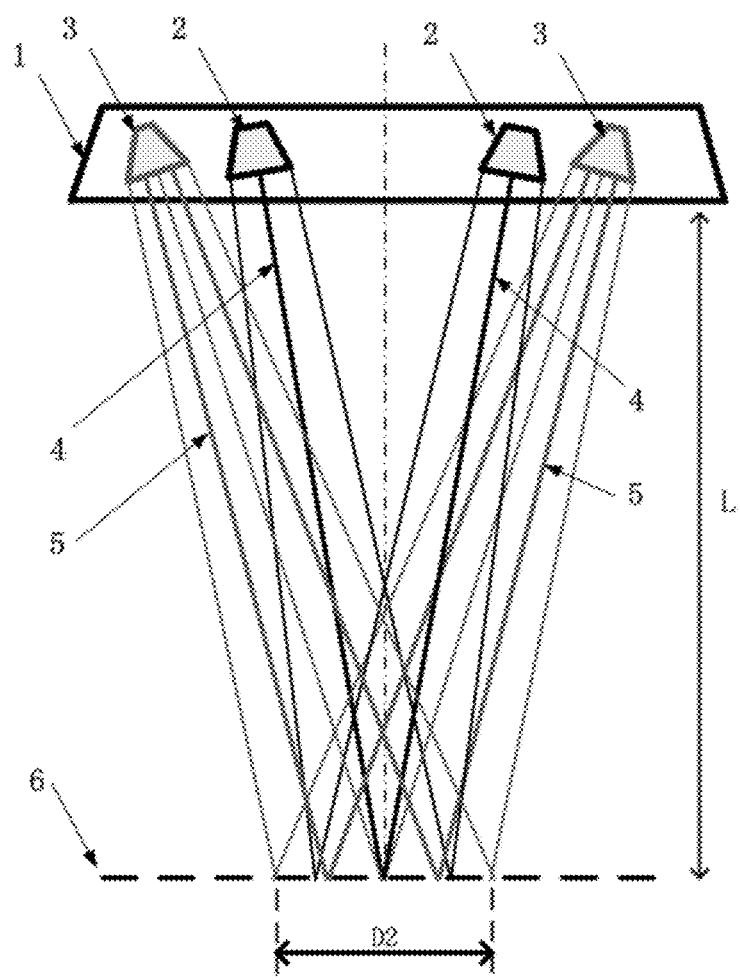
Fig. 5

OPERATING LAMP AND METHOD FOR ADJUSTING OPERATING FIELD LIGHT SPOTS THEREOF

CROSS-REFERENCE TO RELATED APPLICATION

This application is a bypass continuation of Patent Cooperation Treaty Application No. PCT/CN2018/079883, filed on Mar. 21, 2018, the content thereof is hereby incorporated by reference in its entirety.

TECHNICAL FIELD

The present disclosure relates to the technical field of medical instruments, and in particular to an operating lamp and a method for adjusting operating field light spots thereof.

BACKGROUND

In existing operating lamps, a plurality of lighting units are generally provided on lamp holders, the lighting units are disposed at different angles on the lamp holders to provide light beams that are all directed to an operating area but have different emergence angles, and the light beams form one light spot in the operating area.

In clinical practice, different types of operation have different sizes of operating areas. The size of the lighting spot in the operating area needs to be adjusted according to the size of the operating area. If the lighting spot is smaller than the operating area, a part of the operating area is not sufficiently lighted, affecting the operation process. If the lighting spot is much larger than the operating area, since the reflectivity of items, such as sterile drapes and operative instruments, outside the operating area is generally greater than the reflectivity of human tissues, the reflection of these items will cause glare and interfere with the operation process. At the same time, relatively uniform lighting within the operating area is also necessary. Uniform lighting may reduce the discomfort of a doctor and improve the quality of observation by the doctor. Therefore, the ability to adjust the size of the lighting spot in the operating area and the uniformity in the process of adjusting the size of the light spot are critical for operating lamp products.

One solution to change the size of the lighting spot is to change the placement angle of some or all of the lighting units, thereby changing the angle of the light emitted by the lighting units, and thus changing the position on a lighting surface where these lighting units illuminate, so that the intensity distribution of light is changed, and the size of the lighting spot is finally changed. This solution requires a driving mechanism provided inside or outside the lamp holder to adjust the placement angle of the lighting unit or to adjust the angle of a part of the lamp holder. However, the general adjustment process is relatively slow, the driving mechanism is prone to generate noise, and providing the driving mechanism also complicates the structure of the lamp holder.

Another solution is to change the light intensity distribution of a lighting surface by changing the relative intensity of the output light of the lighting unit illuminated at different positions on the lighting surface. In this solution, although the lamp holder has a simple structure and strong reliability, when being adjusted to a large light spot, the peripheral region of the large light spot on the lighting surface is formed only by an individual lighting unit, and in clinical practice, when being adjusted to a large light spot, if the corresponding lighting unit is blocked by the head of the doctor, the lighting spot may be partially darkened.

A further solution is to additionally provide an optical element in an operating lamp so as to adjust the size of the lighting spot through a particular motion of the optical element. Although the adjustment is reliable, the processing and installation process of the optical element is difficult.

SUMMARY

According to various embodiments of the present disclosure, an operating lamp and a method for adjusting operating field light spots thereof are provided, which may satisfy the needs of adjusting the size of lighting spot, and has high reliability and good intensity distribution uniformity during adjustment. In addition, the operating lamp has a simple structure.

An operating lamp, comprising a first lighting unit, a second lighting unit, and a control unit, wherein a light beam emitted by the first lighting unit form a first light spot having a first equivalent diameter in an operating field, and the first light spot have a light distribution that meets an operating lamp standard; a light beam emitted by the second lighting units forms a second light spot having a second equivalent diameter in the operating field, and the second light spot have a light distribution that does not meet the operating lamp standard; the second equivalent diameter is greater than the first equivalent diameter; and the control unit is used for controlling the working states of the first lighting unit and the second lighting unit, and enabling the operating lamp to provide the first light spot or a synthetic light spot having a light distribution that meets the operating lamp standard and is formed by the first light spot and the second light spot.

A method for adjusting operating field light spots of the operating lamp described above, comprising controlling the working states of the first lighting unit and the second lighting unit, enabling the operating lamp to provide the first light spot, or the synthetic light spot having a light distribution that meets an operating lamp standard and is formed by the first light spot and second light spot.

Details of one or more embodiments of the present disclosure are set forth in the accompanying drawings and description below. Other features, objects and advantages of the disclosed systems and methods will be apparent from the description, the drawings and the claims.

BRIEF DESCRIPTION OF THE DRAWINGS

In order to illustrate the technical solutions in the embodiments, a brief introduction to the drawings required for the description of the embodiments or the prior art will be provided below. Obviously, the drawings in the following description are only some of the embodiments, and those of ordinary skill in the art would also be able to obtain other drawings of the embodiments from these drawings.

FIG. 2a is a schematic diagram of a first light beam provided by a first lighting unit in an operating lamp of an embodiment forming a first light spot in an operating field.

FIG. 2b is a schematic diagram of a light field distribution curve of the first light beam shown in FIG. 2a.

FIG. 3a is a schematic diagram of a second light beam provided by a second lighting unit in an operating field in an operating lamp of an embodiment forming a second spot.

FIG. 3*b* is a schematic diagram of a light field distribution curve of the second light beam shown in FIG. 3*a*.

FIG. 4*a* is a schematic diagram of the first lighting unit in an operating lamp of an embodiment being in a lighting state and forming a first light spot in an operating field, and the second lighting unit thereof being in a turn-off state.

FIG. 4*b* is a schematic diagram of a light field distribution curve of the first lighting unit shown in FIG. 4*a*.

FIG. 5 is a schematic diagram of the first lighting units and the second lighting units in an operating lamp of an embodiment both being in a lighting state and forming a synthetic light spot in an operating field.

DETAILED DESCRIPTION OF EMBODIMENTS

Figure 1:
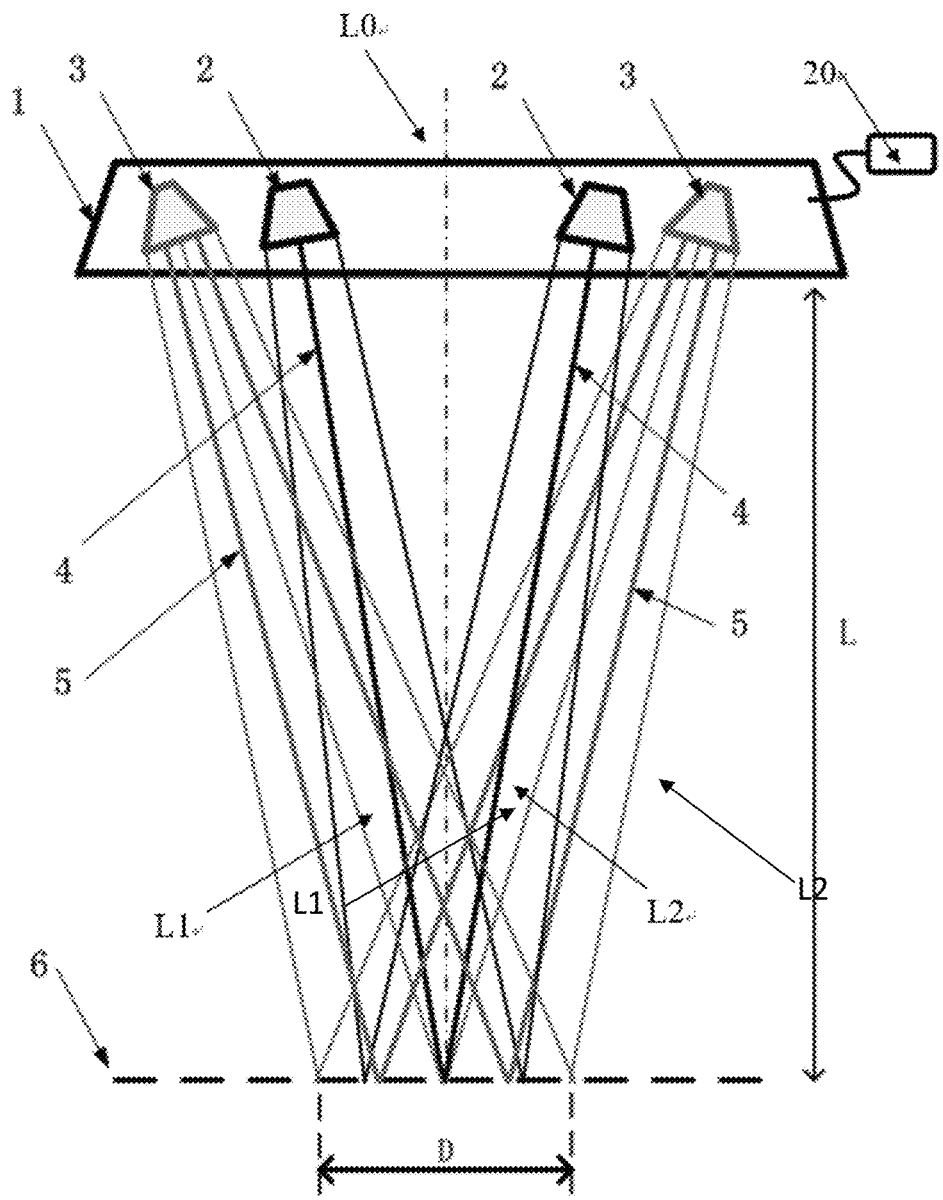
FIG. 1 is a schematic structural diagram of an operating lamp according to an embodiment.

As shown in FIG. 1, an operating lamp provided in an embodiment comprises a lamp holder 1, a first lighting unit 2, a second lighting unit 3, and a control unit 20. The first lighting unit 2 and the second lighting unit 3 are all installed on the lamp holder 1. The control unit 20 is used for controlling the working states of the first lighting unit 2 and the second lighting unit 3. For example, the first lighting unit 2 and the second lighting unit 3 may be controlled to be in a lighting state or a turn-off state. The control unit 20 may be arranged on the lamp holder 1 or on other structures of the operating lamp, for example, on a lamp post (not shown). The control unit 20 may be connected to the first lighting unit 2 and the second lighting units 3 by means of a wired connection or a wireless connection, so as to control the working states of the first lighting unit 2 and the second lighting unit 3.

The lamp holder 1 has an optical axis L0, and the lighting spot provided by the operating lamp is centered on the optical axis L0. The installation positions the first lighting unit 2 and the second lighting unit 3 may be determined according to the optical axis L0. For example, for both the first lighting unit 2 and the second lighting unit 3, a plurality of the first lighting units 2 and a plurality of the second lighting units 3 may be provided, all the first lighting units 2 are symmetrically distributed along the optical axis L0, and all the second lighting units 3 are symmetrically distributed along the optical axis L0. The first lighting unit 2 and the second lighting units 3 may also be uniformly distributed. For example, the plurality of the first lighting units 2 are uniformly arranged on a light emitting surface of the lamp holder 1. The plurality of the second lighting units 3 are uniformly arranged on the light emitting surface of the lamp holder 1. Each of the second lighting units 3 is arranged between any two adjacent first lighting units 2.

The first lighting unit 2 may emit a first light beam 4 when being in a lighting state. The first lighting unit 2 comprises a light source and an optical element cooperating with the light source, wherein the light source and the optical element are relatively fixed and both fixedly installed on the lamp holder 1. The optical element of the first lighting unit 2 is used for shaping the light emitted by the light source of the first lighting unit 2 to provide a suitable and stable first light beam 4.

The second lighting unit 3 may emit a second light beam 5 when being in a lighting state. The second lighting unit 3 also comprises a light source and an optical element cooperating with the light source, wherein the light source and the optical element are relatively fixed and both fixedly installed on the lamp holder 1. The optical element of the second lighting unit 3 is used for shaping the light emitted by the light source of the second lighting unit 3 to provide a suitable and stable second light beam 5.

As shown in FIGS. 2*a* and 2*b*, the first light beam 4 forms a first light spot on a plane where an operating field 6 is located. The distance between the plane where the operating field 6 is located and the light emitting surface of the lamp holder 1 is L. When a plurality of first lighting units 2 are provided, the first light spot formed by the plurality of the first lighting units 2 overlap each other in the operating field 6.

The first light spot has a first equivalent diameter d1. The equivalent diameter referred to in the present disclosure means the diameter of a circumscribed circle of a geometric shape. The so-called circumscribed circle of the geometric shape means a circle that does not exceed any part of the geometric shape and has the most points of intersection with this circle. For example, the circumscribed circle of an ellipse is a circle formed by taking the major axis of the ellipse as the diameter, the circumscribed circle of an irregular polygon means a circle which has the most points of intersection with the vertices of the irregular polygon, provided that the irregular polygon does not exceed the circle.

The equivalent diameter of a light spot may be calculated as needed by specifying the geometric shape formed by points having a specific percentage of maximum intensity on the light spot. For example, the equivalent diameter of the light spot may be determined according to the geometric shape formed by the points having 10% of the maximum intensity on the light spot, and the equivalent diameter of the light spot at this time may be expressed as D10. As another example, the equivalent diameter of the light spot may be determined according to the geometric shape formed by the points having 50% of the maximum intensity on the light spot, and the equivalent diameter of the light spot at this time may be expressed as D50.

The first light spot has a light distribution that meets an operating lamp standard. The operating lamp standard referred to in the present disclosure includes IEC60601-2-41. In some countries, the application of operating lamps also needs to meet standards used in the corresponding countries. For example, in China, operating lamps should also meet an operating shadowless lamp industry standard YY 0627-2008. It should be understood that these standards are all included in the operating lamp standard referred to in the present disclosure.

The shape of the first light spot in the operating field 6 may be a geometric shape such as a circle, an ellipse, a square, a prism, or an irregular polygon. The specific shape is matched according to the shape of the operating field 6, such that the shape of the first light spot may meet the requirement of the lighting range of the operating field 6 during an operation.

The divergence angle of the first light beam 4 is smaller than the divergence angle of the second light beam 5. The first light beam 4 has a first axis L1, and the first axis L1 intersects the optical axis L0 of the lamp holder 1 in the operating field 6. The intensity of the first light spot formed by the first light beam 4 in the operating field 6 is greater in the central region than in the peripheral region, and the intensity distribution is relatively uniform. For example, as shown in FIG. 2b, the first light spot has D10 of 180 mm and D50 of 116 mm, and D50/D10 is 64.4%.

As shown in FIGS. 3a and 3b, the second light beam 5 forms a second light spot on the plane where the operating field 6 is located. When a plurality of the second lighting units 3 are provided, the second light spot formed by the plurality of the second lighting units 3 overlap each other in the operating field 6.

The second light spot has a second equivalent diameter d2. The second equivalent diameter d2 is greater than the first equivalent diameter d1. The second light spot has a light distribution does not meet the operating lamp standard. Therefore, the second light spot is not used to provide lighting to the operating field 6 alone, but to form a synthetic light spot in combination with at least the first light spot and then provide lighting to the operating field 6. The intensity of the second light spot changes from small to large from the center to the periphery, and then from large to small. The maximum intensity of the second light spot is not in the central region, but in the peripheral region adjacent to the central region. The intensity in the central region of the second light spot is less than that in the peripheral region adjacent to the central region. As shown in FIG. 3b, a light field distribution curve of the second light spot has a recessed region 01 at the center or a larger-sized annular region 02 at the center. When lighted by the second light spot alone, an annular light spot or a darker light spot in the central region will be observed.

The shape of the second light spot in the operating field 6 may be a geometric shape such as a circle, an ellipse, a square, a prism, or an irregular polygon. The specific shape is determined according to the shape of the first light spot to enable meeting the requirement of the lighting range of the operating field 6 during an operation after forming a synthetic light spot with the first light spot. As shown in FIG. 1, the second light beam 5 has a second axis L2, and the second axis L2 and the optical axis L0 of the lamp holder 1 intersects in the operating field 6.

When a lighting spot with a smaller diameter is used, the first lighting unit 2 may be driven to be in a lighting state by the control unit 20, and the second lighting units 3 are in a turn-off state. The first light spots provided by all the first lighting units 2 overlap in the operating field 6 to form a superposed first light spot with a smaller diameter. As shown in FIG. 4a, all the first lighting units 2 in the lamp holder 1 are in a lighting state, and a superposed first light spot D1 is formed in the operating field 6; and as shown in FIG. 4b, the shape of a light field distribution curve of the superposed first light spot D1 is similar to a light field distribution curve of the first light spot provided by the first lighting unit 2. In an embodiment, the superposed first light spot D1 has D10 of 180 mm and D50 of 116 mm, and D50/D10 is 64.4%. As shown in FIG. 5, when a lighting spot with a relatively large diameter is used, the first lighting unit 2 and the second lighting unit 3 may be driven to work simultaneously by the control unit 20. The first light spots provided by all the first lighting units 2 overlap in the operating field 6, at the same time the second light spots provided by all the second lighting units 3 also overlap in the operating field 6, and finally, one synthetic light spot D2 is formed by a plurality of the first light spots and a plurality of the second light spots. The synthetic light spot D2 has a light distribution that meets the operating lamp standard.

As the relative intensity of the second lighting units 3 relative to the first lighting unit 2 increases, the light spot diameter of the synthetic light spot D2 gradually increases. During use, a plurality kinds of lighting units with different output intensities may be configured in the lamp holder 1, and two kinds of lighting units with different intensities may output as needed to form a synthetic light spot D2. FIGS. 6, 7, 8, 9 and 10 respectively exemplify, in the cases that the intensity of the second lighting unit 3 is 10%, 25%, 50%, 75%, 100% of the intensity of the first lighting unit 2, a light field distribution curve (long dashed line) formed by the first lighting unit 2 in the operating field 6, a light field distribution curve (dotted line) formed by the second lighting unit 3 in the operating field 6, a synthetic light field distribution curve (dot dashed line) formed by the two, and a synthetic light field distribution normalized curve (solid line).

Figure 6:
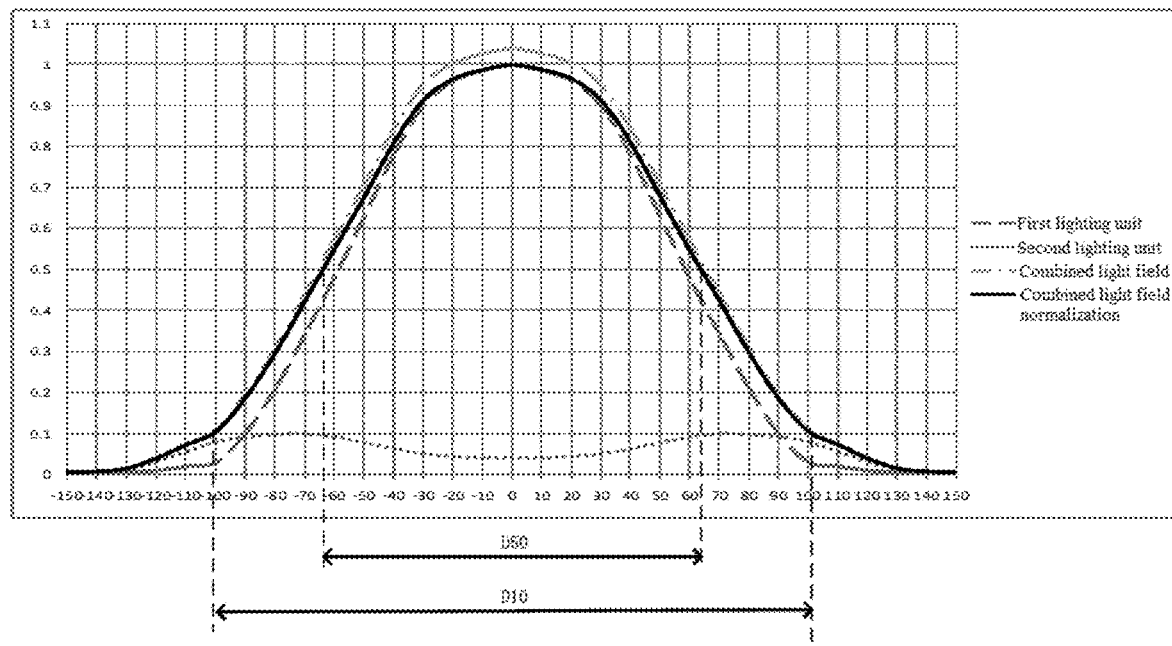
FIG. 6 shows, in the case that the intensity of the second lighting unit is 10% of the intensity of the first lighting unit, a light field distribution curve (long dashed line) formed by the first lighting unit in the operating field, a light field distribution curve (dotted line) formed by the second lighting unit in the operating field, a synthetic light field distribution curve (dot dashed line) formed by the two, and a synthetic light field distribution normalized curve (solid line).
Figure 7:
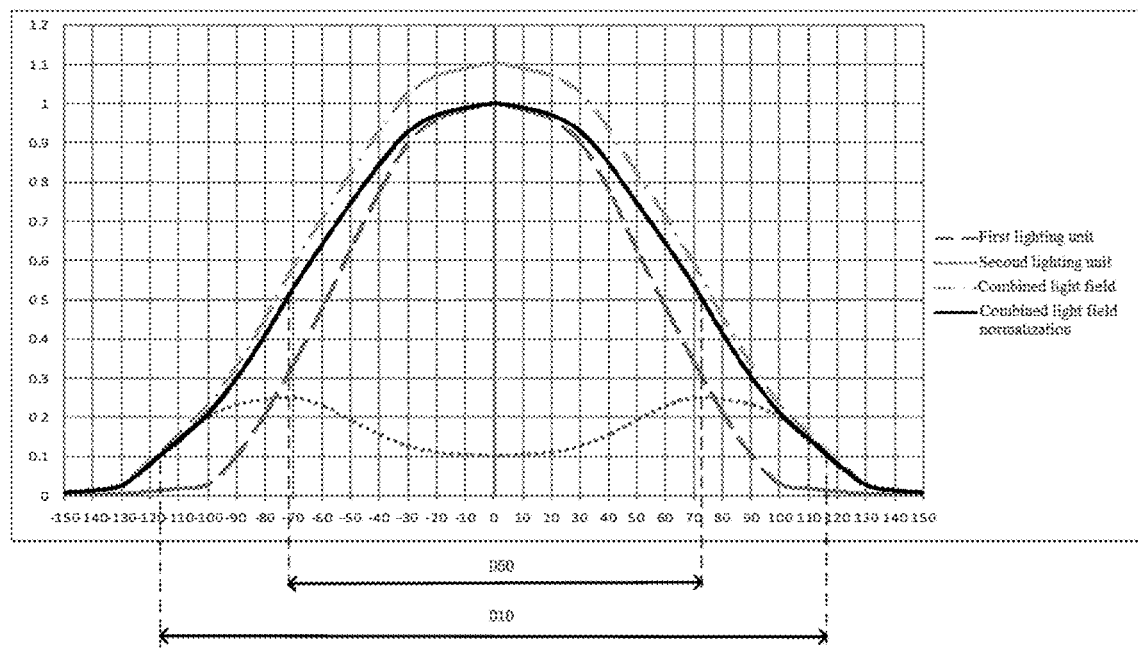
FIG. 7 shows, in the case that the intensity of the second lighting unit is 25% of the intensity of the first lighting unit, a light field distribution curve (long dashed line) formed by the first lighting unit in the operating field, a light field distribution curve (dotted line) formed by the second lighting unit in the operating field, a synthetic light field distribution curve (dot dashed line) formed by the two, and a synthetic light field distribution normalized curve (solid line).
Figure 8:
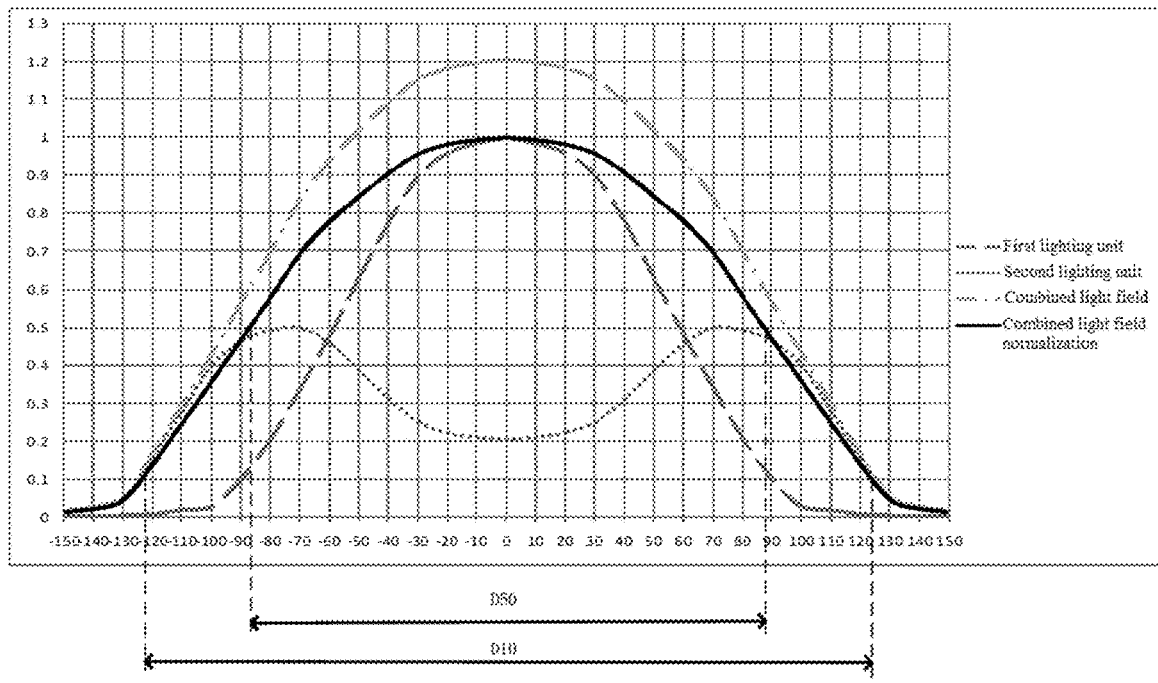
FIG. 8 shows, in the case that the intensity of the second lighting unit is 50% of the intensity of the first lighting unit, a light field distribution curve (long dashed line) formed by the first lighting unit in the operating field, a light field distribution curve (dotted line) formed by the second lighting unit in the operating field, a synthetic light field distribution curve (dot dashed line) formed by the two, and a synthetic light field distribution normalized curve (solid line).
Figure 9:
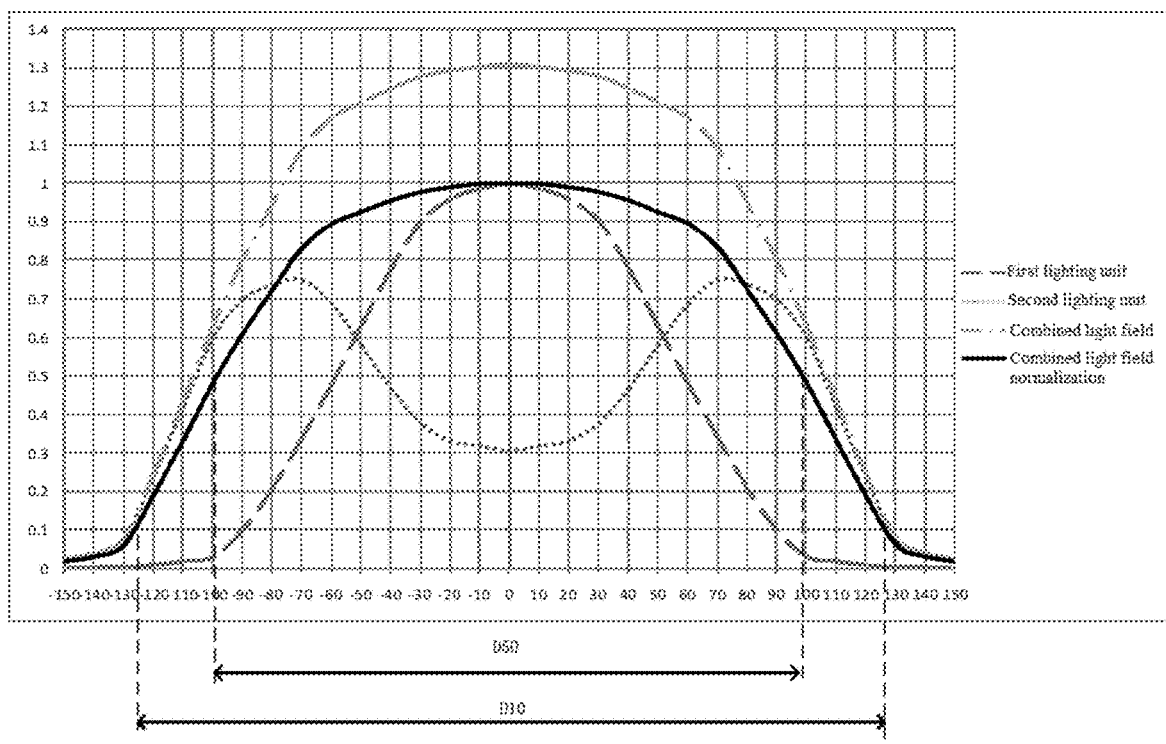
FIG. 9 shows, in the case that the intensity of the second lighting unit is 75% of the intensity of the first lighting unit, a light field distribution curve (long dashed line) formed by the first lighting unit in the operating field, a light field distribution curve (dotted line) formed by the second lighting unit in the operating field, a synthetic light field distribution curve (dot dashed line) formed by the two, and a synthetic light field distribution normalized curve (solid line).
Figure 10:
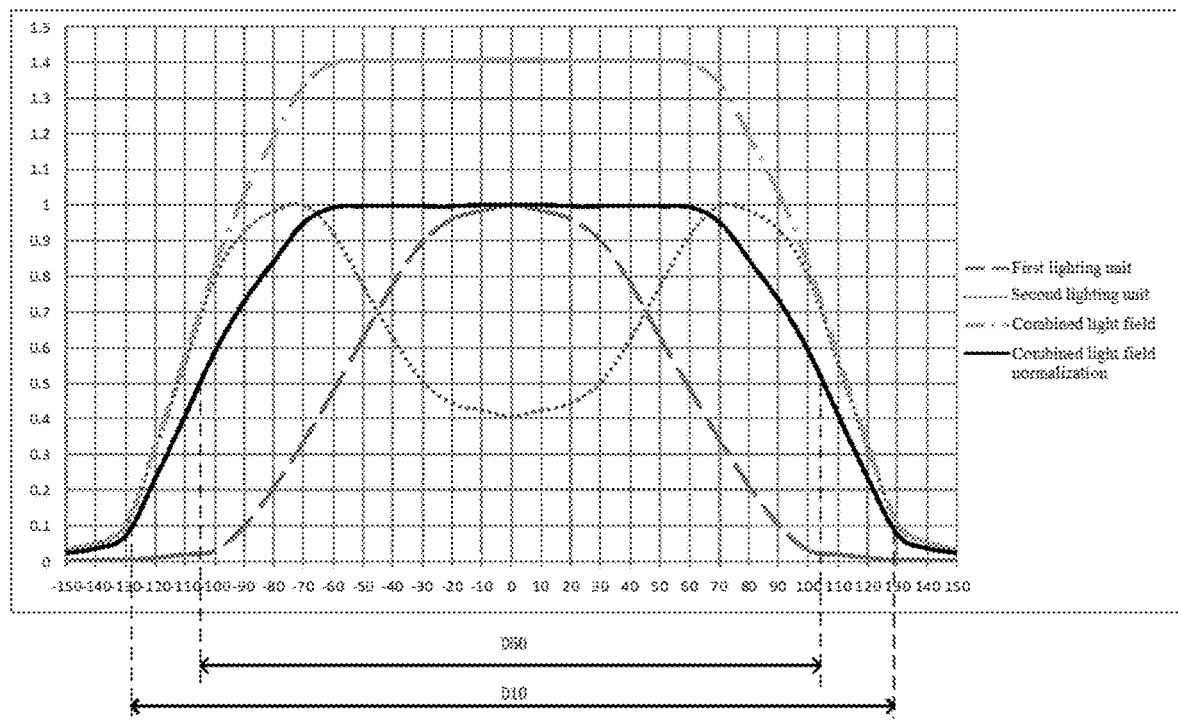
FIG. 10 shows, in the case that the intensity of the second lighting unit is 100% of the intensity of the first lighting unit, a light field distribution curve (long dashed line) formed by the first lighting unit in the operating field, a light field distribution curve (dotted line) formed by the second lighting unit in the operating field, a synthetic light field distribution curve (dot dashed line) formed by the two, and a synthetic light field distribution normalized curve (solid line).

In FIG. 6, for the synthetic light spot D2, D10 is 202 mm, D50 is 128 mm, and D50/D10 is 63.3%. In FIG. 7, for the synthetic light spot D2, D10 is 232 mm, D50 is 144 mm, and D50/D10 is 62%. In FIG. 8, for the synthetic light spot D2, D10 is 246 mm, D50 is 172 mm, and D50/D10 is 69.9%. In FIG. 9, for the synthetic light spot D2, D10 is 252 mm, D50 is 199 mm, and D50/D10 is 79%. In FIG. 10, for the synthetic light spot D2, D10 is 256 mm, D50 is 210 mm, and D50/D10 is 82%.

It can be seen from FIGS. 4b to 10 that for the synthetic light spot D2, D10 increases from 180 mm to 256 mm, and D50 increases from 116 mm to 210 mm. In actual use, the increase in the lighting range of the lighting spot may be clearly perceived, and the uniformity of the lighting spot is also increasing. It can be seen from FIGS. 6, 7, 8, 9 and 10 that the light field distribution curve of the synthetic light spot D2 transitions naturally, the slope changes continuously, and the D50/D10 value is excellent.

The present disclosure may effectively adjust parameters such as the size and uniformity of the synthetic light spot by the common use of the first light spot having the light distribution that meets the operating lamp standard and with a smaller equivalent diameter combined with the second light spot having the light distribution does not meet the operating lamp standard and with a larger equivalent diameter. Compared with the synthesis of two kinds of light spot having different sizes and light distributions both meeting the operating lamp standard, the synthetic light spot formed by the present disclosure does not produce a step change in energy at the boundary of the combination, and the specific performance is that the light field distribution curve of the synthetic light spot D2 transitions naturally, the slope changes continuously, and the D50/D10 value is excellent.

In the specific implementation process, at least two kinds of lighting units or more kinds of lighting units may be selected and used in combination according to the actual light spot size requirements and the adjustment range requirements in clinic.

Figure 13:
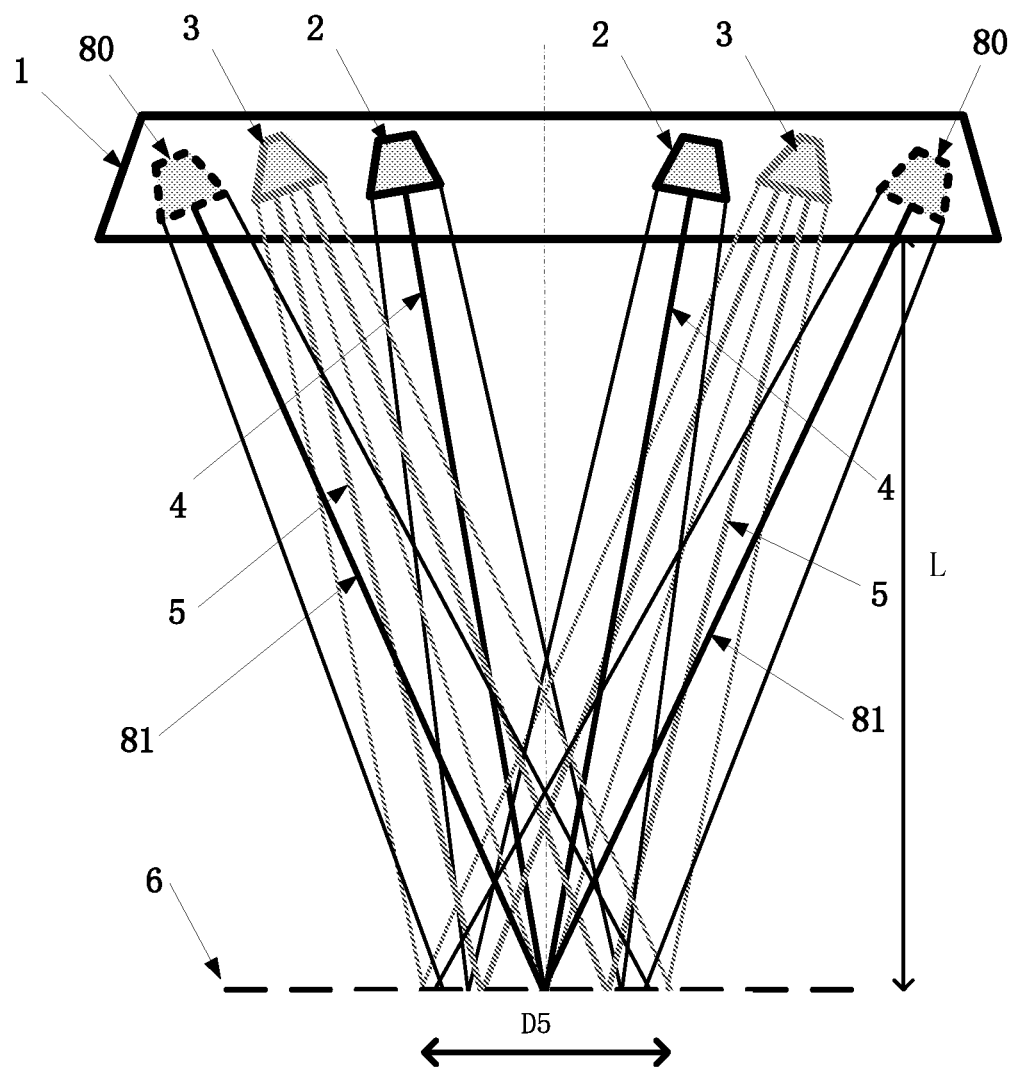
FIG. 13 is a schematic diagram of the first lighting units, the second lighting units, and the third lighting units in an operating lamp of an embodiment all being in a lighting state and forming a synthetic light spot in an operating field.
Figure 13:
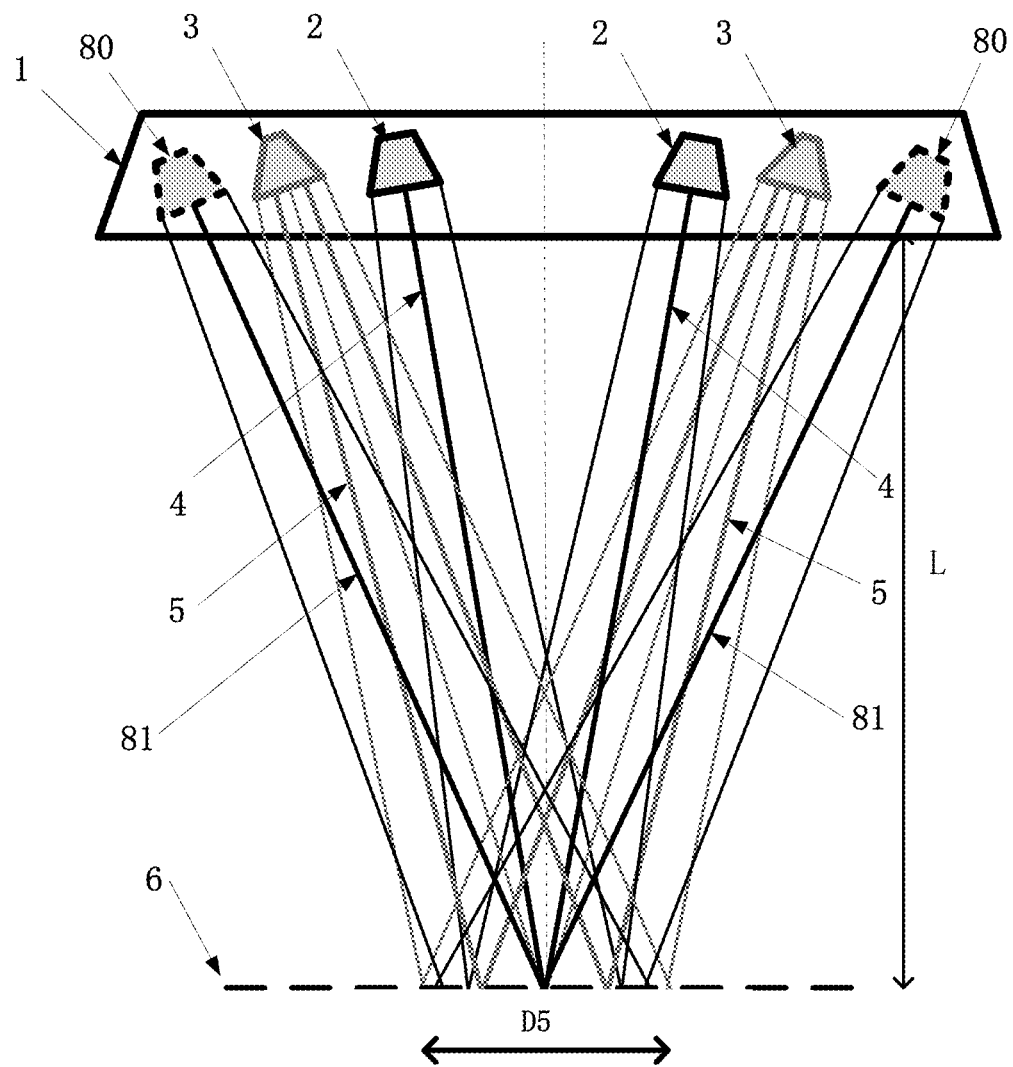

When the adjustment range of the light spot is not large, for example, the synthetic light spot has a final equivalent diameter, and when the final equivalent diameter is 1.5-2 times the first equivalent diameter of the first light spot, two kinds of lighting units may be used. However, if the final equivalent diameter of the synthetic light spot is greater than 2 times the first equivalent diameter of the first light spot, or when the degree of uniformity of the light field is to be higher, three or more kinds of lighting units may be used to make the synthetic light spot more able to meet actual needs. For example, as shown in FIG. 13, a third lighting unit 80 may also be provided. The light beam 81 emitted by the third lighting unit 80 forms a third light spot having a third equivalent diameter D5 in the operating field, the third light spot has a light distribution that does not meet the operating lamp standard, the third equivalent diameter D5 is between the first equivalent diameter and the second equivalent diameter, and the control unit enables the operating lamp to provide a synthetic light spot having a light distribution that meets the operating lamp standard and is formed by the first light spot, the second light spot and the third light spot. The intensity in the central region of the third light spot is less than that in the peripheral region adjacent to the central region. In some embodiments, for the third lighting unit 80, a plurality of the third lighting units are provided, and a third light spot formed by the plurality of the third lighting units overlap each other.

The shape and size, such as D50, D10, of the light field distribution of different lighting units, the slope of the light field distribution curve of different lighting units, the equivalent diameter of the recessed region, the equivalent diameter of the annular area, etc. may also be determined by the actual light spot light field distribution requirements and light field adjustment range in clinic in order to obtain a light field distribution with flexible lighting adjustment, a large adjustment range, and uniform lighting and natural transition throughout the adjustment process.

Figure 11:
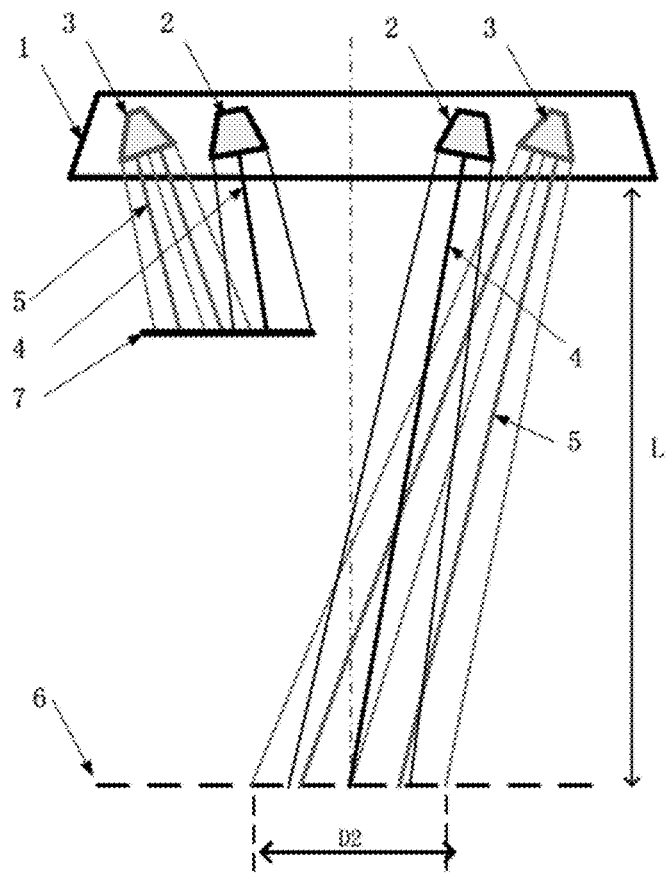
FIG. 11 shows a schematic diagram of a synthetic light spot formed after some of the lighting modules in an operating lamp of an embodiment are blocked.

Still further, in an embodiment, for both the first lighting unit 2 and the second lighting unit 3, a plurality of the first lighting units and a plurality of the second lighting units are provided; one of the plurality of the first lighting units 2 and one of the plurality of the second lighting units 3 correspondingly form a lighting module; and light spots formed by each lighting modules overlap in the operating field 6. These lighting modules are uniformly distributed in the lamp holder 1, and the light spots formed by the plurality of lighting modules are superposed again to form a final synthetic light spot. As long as these lighting modules are not completely blocked, there will be no shadow, and the shape and relative distribution of the lighting field in the operating field will not change. As shown in FIG. 11, when an object 7, for example the head of a doctor, blocks one side of the light emitting surface of the lamp holder 1, the synthetic light spot D2 formed by the unblocked lighting module on the other side thereof still illuminates the original operating field.

Figure 12A:
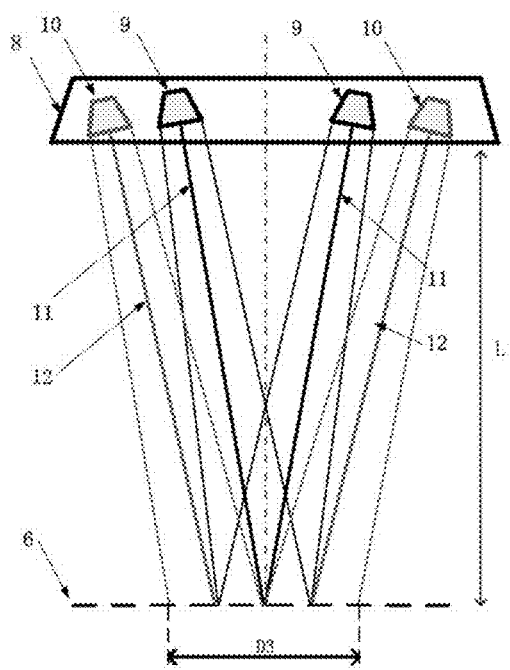
FIG. 12*a* shows a schematic view of a synthetic light spot provided by an existing operating lamp.
Figure 12B:
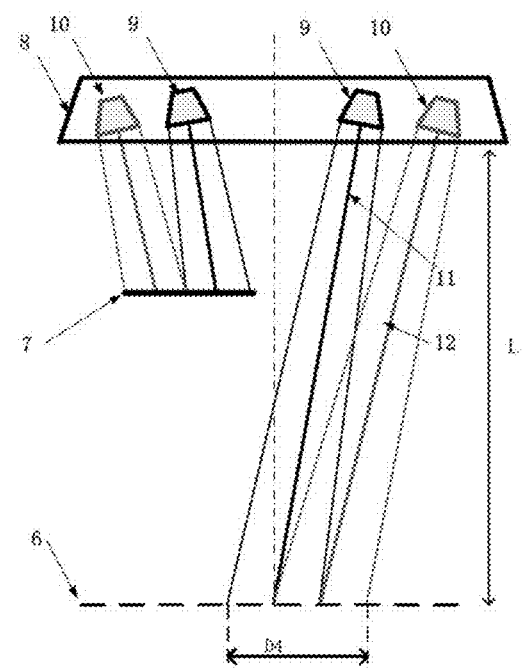
FIG. 12*b* shows a schematic diagram of a synthetic light spot formed after some of the lighting units of the operating lamp in FIG. 12*a* are blocked.

In order to reflect the advantages of the above solution, an existing solution is shown in FIG. 12a. A lamp holder 8 comprises therein a lighting unit 9 for lighting a central portion of an operating field 6 and a lighting unit 10 for lighting a peripheral portion of the operating field 6, which cooperate on the operating field 6 to form a light spot D3. As shown in FIG. 12b, when an object 7 blocks one side of the lamp holder 8, the light emitted by the lighting unit corresponding to this side is blocked, and the lighting field of the operating field 6 is changed to form a light spot D4. It can be seen that the shapes and relative distribution positions of the light spot D3 and D4 are changed, which may cause the shadow region or the region with significantly uneven lighting to be present in the operating field, thereby affecting the operation process.

It can be understood from the foregoing description that the solution provided by the present disclosure has more obvious advantages than the existing solutions when lighting with a relatively large light spot.

The present disclosure further provides a method for adjusting operating field light spots of the above-mentioned operating lamp, comprising enabling the operating lamp to provide first light spot or synthetic light spot having a light distribution that meets an operating lamp standard and is formed by the first light spot and second light spot by means of controlling the working states of the first lighting unit 2 and the second lighting unit 3. For example, when lighting with a relatively small light spot is used, the first lighting unit 2 may be controlled to be in a lighting state, while other lighting units such as the second lighting units 3 are in a turn-off state to enable the first lighting unit 2 to provide the first light spot having the light distribution that meets the operating lamp standard as the light spot. When lighting with a relatively large light spot is used, the first lighting unit 2 and the second lighting unit 3 may be controlled to be in a lighting state, such that the first light spot and the second light spot form the synthetic light spot as the light spot.

Controlling the working states of the first lighting unit 2 and the second lighting unit 3 comprises adjusting the relative intensity of the first light spot formed by the first lighting unit 2 and the second light spot formed by the second lighting units 3. For example, the output power of the first lighting unit 2 and the second lighting unit 3 may be adjusted such that the respective output intensity is changed. In some further embodiments, second lighting units 3 having a plurality of intensity outputs can also be provided, and at the same time first lighting unit 2 having a plurality of intensity outputs can also be provided. An appropriate intensity combination may be selected as needed to make the second lighting unit 3 and the first lighting unit 2 work together to form a synthetic light spot.

In some embodiments, in order to enlarge the equivalent diameter of the synthetic light spot formed by the first light spot and the second light spot, the relative intensity of the second light spot formed by the second lighting unit 3 may be increased. In some embodiments, in order to enlarge the equivalent diameter of the synthetic light spot formed by the first light spot and the second light spot, the relative intensity of the first light spot formed by the first lighting unit 2 may also be reduced. In further some embodiments, in order to enlarge the equivalent diameter of the synthetic light spot formed by the first light spot and the second light spot, it is also possible to reduce the relative intensity of the first light spot formed by the first lighting unit 2 while increasing the relative intensity of the second light spot formed by the second lighting unit 3.

In some embodiments, a third lighting unit can also be provided. The light beam emitted by the third lighting unit forms a third light spot having a third equivalent diameter in an operating field, the third light spot has a light distribution that does not meet the operating lamp standard, the third equivalent diameter is between a first equivalent diameter and a second equivalent diameter, and a synthetic light spot having a light distribution that meets the operating lamp standard and is formed by the first light spot, the second light spot and the third light spot. The size of the synthetic light spot formed by the first light spot, the second light spot and the third light spot is adjusted by means of adjusting the relative intensity of the first light spot formed by the first lighting unit, the second light spot formed by the second lighting unit, and the third light spot formed by the third lighting unit. This solution has more obvious advantages when lighting with a relatively large light spot is provided, for example, when the equivalent diameter of the synthetic light spot is greater than 2 times the first equivalent diameter of the first light spot provided by the first lighting unit 2, or when the degree of uniformity of the light field is higher.

What is claimed is:

1. An operating lamp, comprising:
   a first lighting unit, wherein a light beam emitted by the first lighting unit forms a first light spot having a first equivalent diameter in an operating field, wherein an intensity in a central region of the first light spot is greater than that in a peripheral region adjacent to the central region;
   a second lighting unit, wherein a light beam emitted by the second lighting unit forms a second light spot having a second equivalent diameter in the operating field, wherein an intensity in a central region of the second light spot is less than that in a peripheral region adjacent to the central region, wherein the second equivalent diameter is greater than the first equivalent diameter; and
   a control unit, configured to control working states of the first lighting unit and the second lighting unit, wherein the control unit turns on the first lighting unit and turns off the second lighting unit to enable the operating lamp to provide the first light spot or turns on both the first lighting unit and the second lighting unit to enable the operating lamp to provide a synthetic light spot having a light distribution formed by the first light spot and the second light spot, wherein an intensity in a central region of the synthetic light spot is greater than that in a peripheral region adjacent to the central region.

2. The operating lamp of claim 1, further comprising a lamp holder for fixed installation of the first lighting unit and the second lighting unit, wherein the lamp holder has an optical axis, the light beam emitted by the first lighting unit has a first axis, and the light beam emitted by the second lighting unit has a second axis, the first axis, the second axis and the optical axis of the lamp holder intersect in the operating field.

3. The operating lamp of claim 2, wherein the first lighting unit comprises a plurality of lighting units and the second lighting unit comprises a plurality of lighting units, and a plurality of first light spots formed by the plurality of the first lighting units overlap in the operating field, and a plurality of second light spots formed by the plurality of the second lighting units overlap in the operating field.

4. The operating lamp of claim 3, wherein the plurality of the first lighting units are uniformly arranged on a light emitting surface of the lamp holder, and one of the plurality of the second lighting units is arranged between any two adjacent first lighting units.

5. The operating lamp of claim 1, wherein the first lighting unit comprises a plurality of lighting units and the second lighting unit comprises a plurality of lighting units, one of the plurality of the first lighting units and one of the plurality of the second lighting units correspondingly form a lighting module, and light spots formed by each lighting module overlap in the operating field.

6. The operating lamp of claim 1, wherein the synthetic light spot has a final equivalent diameter, and the final equivalent diameter is smaller than or equal to 1.5-2 times the first equivalent diameter.

7. The operating lamp of claim 1, further comprising a third lighting unit, wherein a light beam emitted by the third lighting unit forms a third light spot having a third equivalent diameter in the operating field, wherein an intensity in a central region of the third light spot is less than that in a peripheral region adjacent to the central region, the third equivalent diameter is between the first equivalent diameter and the second equivalent diameter, and the control unit enables the operating lamp to provide the synthetic light spot formed by the first light spot, the second light spot and the third light spot, wherein an intensity in a central region of the synthetic light spot is greater than that in a peripheral region adjacent to the central region.

8. The operating lamp of claim 7, wherein the third light unit comprises a plurality of lighting units, and a plurality of third light spots formed by the plurality of the third lighting units overlap in the operating field.

9. The operating lamp of claim 7, wherein
   the first lighting unit comprises a plurality of lighting units, the second lighting unit comprises a plurality of lighting units and the third lighting unit comprises a plurality of lighting units;
   one of the plurality of the first lighting units, one of the plurality of the second lighting units and one of the plurality of the third lighting units form a lighting module; and
   light spots formed by each lighting modules overlap in the operating field.

10. A method for adjusting light spots in an operating field of an operating lamp, comprising:
   controlling the working states of a first lighting unit and a second lighting unit of the operating lamp, wherein a light beam emitted by the first lighting unit forms a first light spot having a first equivalent diameter in the operating field, wherein an intensity in a central region of the first light spot is greater than that in a peripheral region adjacent to the central region, wherein a light beam emitted by the second lighting unit forms a second light spot having a second equivalent diameter in the operating field, wherein an intensity in a central region of the second light spot is less than that in a peripheral region adjacent to the central region, wherein the second equivalent diameter is greater than the first equivalent diameter; and turning on the first lighting unit and turning off the second lighting unit to enable the operating lamp to provide the first light spot, or turning on both the first lighting unit and the second lighting unit to enable the operating lamp to provide a synthetic light spot having a light distribution formed by the first light spot and the second light spot, wherein an intensity in a central region of the synthetic light spot is greater than that in a peripheral region adjacent to the central region.

11. The method of claim 10, wherein controlling the working states of the first lighting unit and the second lighting unit comprises respectively adjusting relative intensities of the first light spot formed by the first lighting unit and the second light spot formed by the second lighting unit.

12. The method of claim 10, further comprising increasing the relative intensity of the second light spot formed by the second lighting unit, or reducing the relative intensity of the first light spot formed by the first lighting unit, so as to enlarge the equivalent diameter of the synthetic light spot formed by the first light spot and the second light spot.

13. The method of claim 10, further comprising:
adjusting a size of a synthetic light spot formed by the first light spot, the second light spot and a third light spot, by adjusting relative intensities of the first light spot formed by the first light unit, the second light spot formed by the second lighting unit and the third light spot formed by a third lighting unit, wherein the light beam emitted by the third lighting unit forms the third light spot having the third equivalent diameter in the operating field, wherein an intensity in a central region of the third light spot is less than that in a peripheral region adjacent to the central region, the third equivalent diameter is between the first equivalent diameter and the second equivalent diameter, and the synthetic light spot formed by the first light spot, the second light spot and the third light spot, wherein an intensity in a central region of the synthetic light spot is greater than that in a peripheral region adjacent to the central region.

14. An operating lamp, comprising:
a first lighting unit, wherein a light beam emitted by the first lighting unit forms a first light spot having a first equivalent diameter in an operating field, wherein an intensity in a central region of the first light spot is greater than that in a peripheral region adjacent to the central region;
a second lighting unit, wherein a light beam emitted by the second lighting unit forms a second light spot having a second equivalent diameter in the operating field wherein an intensity in a central region of the second light spot is less than that in a peripheral region adjacent to the central region, wherein the second equivalent diameter is greater than the first equivalent diameter; and
a control unit configured to control working states of the first lighting unit and the second lighting unit, and enable the operating lamp to provide a synthetic light spot having a light distribution formed by the first light spot and the second light spot, wherein an intensity in a central region of the synthetic light spot is greater than that in a peripheral region adjacent to the central region.

15. The operating lamp of claim 14, wherein the first light spot has a geometric center, the second light spot has a geometric center, the geometric center of the first light spot and the geometric center of the second light spot overlap in the operating field.

16. The operating lamp of claim 14, further comprising a lamp holder for fixed installation of the first lighting unit and the second lighting unit, wherein the first lighting unit distributes dispersedly on a light emitting surface of the lamp holder, the second lighting unit distributes dispersedly on the light emitting surface of the lamp holder.

17. The operating lamp of claim 14, wherein a light field distribution curve in the operating field formed by the first lighting unit has one peak, a light field distribution curve in the operating field formed by the second lighting unit has two peaks and a trough between the two peaks.

* * * * *